(12) United States Patent
Staud

(10) Patent No.: US 6,277,955 B1
(45) Date of Patent: Aug. 21, 2001

(54) MATERIALS AND METHOD FOR THE DETECTION AND TREATMENT OF WEGENER'S GRANULOMATOSIS

(75) Inventor: Roland Staud, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/472,579

(22) Filed: Dec. 27, 1999

Related U.S. Application Data

(63) Continuation of application No. 08/953,327, filed on Oct. 17, 1997, now Pat. No. 6,033,915
(60) Provisional application No. 60/028,701, filed on Oct. 18, 1996.

(51) Int. Cl.$^7$ .................................................. A61K 38/04
(52) U.S. Cl. .................... 530/327; 530/328; 530/329; 530/330; 530/331; 435/810
(58) Field of Search .................... 530/327, 328, 530/329, 330, 331; 435/810

(56) References Cited

U.S. PATENT DOCUMENTS 5,200,319 * 4/1993 Arnaout et al. ................. 435/7.24

FOREIGN PATENT DOCUMENTS 9200378    1/1992  (WO) .

OTHER PUBLICATIONS

Williams, Jr., Ralph C., Roland Staud, Christine C. Malone, Joel Payabyab, Laura Byres, Dennis Underwood (1994) "Epitopes on Proteinase=3 Recognized by Antibodies from Patients with Wegener's Granulomatosis" *Journal of Immunology* 152:4722–4737.

Campanelli, David, Maxine Melchoir, Yiping Fu, Munehiro Nakata, Howard Shuman, Carl Nathan, Joelle E. Gabay (1990) "Cloning of cDNA for Proteinase 3: A Serine Protease, Antibiotic, and Autoantigen from Human Neutrophilis" *J. Exp. Med.* 172:1709–1715.

Blockmans et al. (1998) *Annals of the Rheumatic Disease* 57:141–145.

\* cited by examiner

*Primary Examiner*—Patrick Nolan
(74) *Attorney, Agent, or Firm*—Saliwanchik, Lloyd & Saliwanchik

(57) ABSTRACT

The subject invention pertains to the identification of peptides useful in the detection and treatment of Wegener's granulomatosis.

3 Claims, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Ile Cys Asp Gly Ile Ile Gln Gly Ile Asp Ser
1               5                   10

(2) INFORMATION FOR SEQ ID NO:2:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Ala His Cys Leu Arg Asp Ile Pro Gln Arg Leu
1               5                   10

(2) INFORMATION FOR SEQ ID NO:3:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

Leu Arg Asp Ile Pro Gln Arg Leu Val Asn Val
1               5                   10

MATERIALS AND METHOD FOR THE DETECTION AND TREATMENT OF WEGENER'S GRANULOMATOSIS

CROSS-REFERENCE TO RELATED APPLICATION

This application is a continuation of application U.S. Ser. No. 08/953,327; filed Oct. 17, 1997, now U.S. Pat. No. 6,033,915; and claims the benefit of U.S. Provisional Application No. 60/028,701, filed Oct. 18, 1996.

BACKGROUND OF THE INVENTION

Autoimmune diseases are characterized by an abnormal immune response (involving either immune system cells or antibodies) directed against normal autologous (self) tissues. Autoimmune diseases afflict huge numbers of individuals throughout the world.

A normal immune system has the capacity to identify and destroy a large variety of foreign invader organisms such as bacteria and viruses. Remarkably, a normal immune system can readily distinguish foreign substances from self, and thereby is able to react vigorously against potentially pathogenic entities from the environment without harming the host's own cells.

The immune system's non-reactivity to self is termed immunological tolerance. In pathological situations, immunological tolerance to a wide variety of self substances is broken, resulting in an autoimmune response to self. If of an appropriate nature and of sufficient severity and duration, the anti-self response will result in an autoimmune disease. In certain autoimmune diseases, specific elements of the immune system predominate in mediating the pathogenic process, while in other autoimmune diseases, all of the components of the immune system cooperate to produce disease. Antibodies are considered to play the major causal roles in diseases such as systemic lupus erythematosus, myasthenia gravis and Graves' disease, while cellular immune mechanisms are believed to be those primarily involved in multiple sclerosis (MS) and insulin dependent diabetes (IDD).

A number of strategies have been used or proposed to suppress autoimmune diseases, most notably drugs, such as cyclophosphamide, cyclosporin A, methotrexate, and Imuran (azathioprine). Steroid compounds, such as prednisone and methylprednisolone, are also employed in many instances. These drugs have limited long term efficacy against both cell- and antibody-mediated autoimmune diseases. Use of such drugs is limited by virtue of their toxic side effects which include "global" immunosuppression. Prolonged treatment with these drugs inhibits the normal protective immune response to pathogenic microorganisms, thereby increasing the risk of infections. A further drawback is that immune-mediated elimination of aberrant cells is impaired and there is, thus, an increased risk that malignancies will develop in patients receiving prolonged global immunosuppression.

Known autoimmune disorders include diabetes, multiple sclerosis, autoimmune uveitis, rheumatoid arthritis, Addison's disease, thyroiditis, atrophic gastritis, myasthenia gravis, idiopathic thrombocytopenic purpura, hemolytic anemia, systemic lupus erythematosus, primary biliary cirrhosis, Wegener's granulomatosis, polyarteritisnodosa, and inflammatory bowel disease.

Wegener's granulomatosis (WG) is characterized by necrotizing granulomatous lesions of the respiratory tract, glomerulonephritis, and, frequently, vasculitis involving other organs. WG is known to be rare, but the exact annual incidence of WG in the general population is not known. Although the incidence of WG is quite low, the syndrome has been observed in persons aged 3 months to 75 years; the peak incidence is in the fourth and fifth decades.

The exact cause of WG is unknown. The clinical course of WG, with initial respiratory tract involvement and then later glomerulonephritis, suggests a possible chain of events in which a pathogenic agent gains entry to the respiratory tract and elicits an inflammatory response that later extends to other tissues.

The differentiation of Wegener's granulomatosis from those diseases that present with similar histopathologic findings is important because management may be different. Infections, especially those with Mycobacterium, Nocardia, or fungi, must be ruled out.

In the early 1980s, researchers described the presence of antibodies directed against cytoplasmic components of neutrophils in patients with segmental necrotizing glomerulonephritis and systemic vasculitis. The presence of these anticytoplasmic antibodies in WG has been reported. These antibodies in the serum of patients with WG cause a characteristic cytoplasmic granular staining pattern by immunofluorescence. These antibodies are called antineutrophil cytoplasmic antibodies (ANCAs). The term c-ANCA is used for cytoplasmic staining antineutrophil cytoplasmic antibody, and p-ANCA for perinuclear staining antineutrophil cytoplasmic antibody.

ANCAs are important in the diagnosis of patients with necrotizing, granulomatous vasculitis, particularly Wegener's granulomatosis (WG). The specificity c-ANCAs is high for the presence of WG (up to 90%). c-ANCAs are directed against proteinase-3 (PR-3), a serine proteinase, found in azurophilic granules of human neutrophils. PR-3 consists of 228 amino acids and has a molecular weight of 29 kD. The most utilized method for detection of ANCAs is indirect immunofluorescence (IIF) using ethanol-fixated human neutrophils as substrate. However, a significant number of false positive and false negative results have been described with this method. In order to achieve greater diagnostic specificity, anti-PR-3 ELISAs have been utilized. However, all extraction procedures for PR-3 from azurophilic granules, including reverse HPLC, have been troubled with impurities, particularly lactoferrin, which make PR-3 ELISAs less specific. Also, it is relatively difficult and expensive to purify PR-3; therefore, an alternative method for detecting the autoantibodies would be helpful.

The amino acid sequence of the PR-3 protein is known and attempts have been made to produce it recombinantly. See, for example, Campanelli, D., M. Melchior, Y. Fu, M. Nakata, H. Shuman, C. Nathan, J. E. Gabay (1990)*J. Exp. Med* 172:1709 –1715. So far, the recombinantly produced protein has not performed satisfactorily in the assays for WG. Another problem that is inherent in the use of the full-length PR-3 protein is that this protein is a highly active protease which degrades other proteins as well as itself. The strong protease activity of this protein makes it difficult to work with.

BRIEF SUMMARY OF THE INVENTION

The subject invention pertains to the identification of peptides which are useful in an assay for detecting the autoimmune disease known as Wegener's granulomatosis (WG).

Specifically, the subject invention pertains to peptide fragments of the full-length PR-3 protein which can be used in an assay to detect autoantibodies associated with WG. These peptides are easy and inexpensive to manufacture and are, therefore, advantageous compared to the current use of the full-length purified PR-3 protein. These peptides can also be used in the treatment of WG.

BRIEF DESCRIPTION OF THE SEQUENCES

SEQ ID NO. 1 is synthetic peptide PR3-5 according to the subject invention.

SEQ ID NO. 2 is synthetic peptide PR3-8 according to the subject invention.

SEQ ID NO. 3 is synthetic peptide PR3-11 according to the subject invention.

DETAILED DISCLOSURE OF THE INVENTION

The subject invention concerns the identification of PR-3 peptides which react with high sensitivity with c-ANCA-positive sera from patients with WG. Three peptides, each 11 amino acids long, are specifically exemplified herein. These peptides have been synthesized in our protein core laboratory. The purity of these PR-3 peptides was found to be >99% by HPLC.

The identified peptides are:

PR3-5: Ile-Cys-Asp-Gly-Ile-Ile-Gln-Gly-Ile-Asp-Ser (SEQ ID NO. 1)

PR3-8: Ala-His-Cys-Leu-Arg-Asp-Ile-Pro-Gln-Arg-Leu (SEQ ID NO. 2)

PR3-1: Leu-Arg-Asp-Ile-Pro-Gln-Arg-Leu-Val-Asn-Val (SEQ ID NO. 3)

Those skilled in the art, having the benefit of the instant disclosure, could make minor modifications to the exemplified peptides without departing from the scope of the instant invention. Such minor modifications would include, for example, adding a small number of amino acids, corresponding to the PR-3 protein, to one or both ends of the peptides.

The peptides of the subject invention can be used in standard assays to detect the onset, or monitor the progression of, WG. Also, as described herein, the peptides can be used to distinguish between classical WG and limited WG. The clinical differences between these forms of WG are known to those skilled in the art but, until now, there has been no diagnostic test to readily distinguish between these conditions, particularly at an early stage of development.

The peptides of the subject invention can be used in standard ELISA or RIA assays. These assays, as well as other assays useful for detecting antibodies, are well known and readily utilized by those skilled in the art.

A further embodiment of the subject invention concerns the use of the PR-3 peptides of the subject invention as part of a diagnostic assay which tests for any one, or all, of a panel of antigens. In a preferred embodiment, such a panel may include antigens associated with other autoimmune conditions. Such antigens are exemplified in Table 1. Other such antigens would be known to those skilled in the art.

The peptides of the subject invention can also be used by those skilled in the art to prevent or reduce the severity of WG. Methods of administering peptides as an immunotherapy composition are well known to those skilled in the art. See, for example, Milich, *Advances in Immunology*, Vol. 45, 1989; and Fundenberg et al., *Basic and Clinical Immunology*, Chapter 17, 1980.

TABLE 1

| Condition | Antigens |
|---|---|
| Multiple Sclerosis | myelin basic protein |
|  | proteolipid protein |
| Rheumatoid Arthritis | collagen |
| Lupus | DNA |
|  | histone proteins |
| IDDM | GAD |
|  | insulin |
|  | IA-2 |
|  | IA-2β |
|  | 38 kD protein |
|  | perforin |
| Thyroid | thyroglobulin |
|  | peroxidase |
| Vitiligo | tyrosinase |

Following are examples which illustrate procedures for practicing the invention. These examples should not be construed as limiting. All percentages are by weight and all solvent mixture proportions are by volume unless otherwise noted.

EXAMPLE 1

Detection of Wegener's Granulomatosis Using PR-3 Peptides

The peptides were linked to ELISA plates by pre-coating plates with 200 μl/well polyalanine/polylysine(poly(A-K), Sigma Chemical Co., St. Louis, Mo.) at a concentration of 20 mg/ml in 0.1 M NaHCO$_3$ (pH 9.0). After being washed three times, the peptides were fixed to the poly(A-K) pre-coated plates by using the peptides, which had been dissolved in 0.125% (v/v) glutaraldehyde at a final concentration of 0.1 mg/ml. After 1 hour incubation, the plates were washed three times, then blocked with 2% BSA-PBS for 1 hour. After PR-3 peptides were fixed to the ELISA plates, a 1:1000 dilution of WG sera or control sera was added to the plates and the ELISA was completed by using F(ab')2 peroxidase-conjugated goat anti-human IgG.

Results of these experiments are shown in Table 2.

TABLE 2

| | PR-3 peptide ELISA | | |
|---|---|---|---|
| Diagnosis | cANCA pos. sera | PR-3 | PR-3 peptides |
| Wegener's granulomatosis | 13 | 11 | 9 |
| Systemic lupus erythematosus | 1 | 0 | 0 |
| Rheumatoid arthritis | 1 | 0 | 1 |
| Ulcerative colitis | 3 | 0 | 3 |
| Behcet's disease, CNS vasculitis, serum sickness | 3 | 0 | 2 |
| Others | 7 | 3 | 4 |
| Total | 28 | 14 | 19 |

EXAMPLE 2

Use of PR-3 Peptides to Distinguish Between Classic Wegener's Granulomatosis and Limited Wegener's Granulomatosis As shown in Tables 3 and 4, the peptides of the subject invention can be used advantageously to differentiate between classic WG and limited WG.

TABLE 3

| | PR-3 peptide ELISA in WG patients | | | |
|---|---|---|---|---|
| Diagnosis | Patients | cANCA | PR-3 | PR-3 peptides |
| Classic WG | 9 | 9 | 8 | 8 |
| Limited WG | 4 | 4 | 3 | 1 |
| Total | 13 | 13 | 11 | 9 |

TABLE 4

| | Peptide ELISA in WG patients | | | |
|---|---|---|---|---|
| Diagnosis | cANCA | Peptide-5 | Peptide-8 | Peptide-11 |
| Classic WG | 9 | 1 | 3 | 5 |
| Limited WG | 4 | 0 | 1 | 1 |
| Total | 13 | 1 | 4 | 6 |

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A peptide of human proteinase-3 consisting of an amino acid sequence selected from the group consisting of SEQ ID NO. 1, SEQ ID NO. 2 and SEQ ID NO. 3, or a fragment thereof, wherein said peptide or fragment is immunoreactive with antineutrophil cytoplasmic antibodies.

2. A kit for detecting antibodies that are immunoreactive with an antigen associated with an autoimmune condition, said kit comprising in one or more containers a peptide of human proteinase-3, wherein said peptide consists of an amino acid sequence selected from the group consisting of SEQ ID NO. 1, SEQ ID NO. 2 and SEQ ID NO. 3, or a fragment thereof, and wherein said peptide or fragment is immunoreactive with antineutrophil cytoplasmic antibodies.

3. The kit according to claim 2, wherein said kit further comprises an antigen associated with an autoimmune disease selected from the group consisting of multiple sclerosis, rheumatoid arthritis, systemic lupus erythematosus, insulin dependent diabetes, myasthenia gravis, Grave's disease, and vitiligo.

* * * * *

UNITED STATES PATENT AND TRADEMARK OFFICE
CERTIFICATE OF CORRECTION

PATENT NO. : 6,277,955 B1
DATED : August 21, 2001
INVENTOR(S) : Roland Staud

It is certified that error appears in the above-identified patent and that said Letters Patent is hereby corrected as shown below:

Column 2,
Lines 52-53, "(1990)*J. Exp. Med*" should read -- (1990) *J. Exp. Med.* --.

Column 3,
Line 33, "PR3-1:" should read -- PR3-11: --.
Line 67, "17,1980." should read -- 17, 1980. --.

Signed and Sealed this

Twelfth Day of March, 2002

Attest:

*Attesting Officer*

JAMES E. ROGAN
*Director of the United States Patent and Trademark Office*